United States Patent [19]

Gönczi et al.

[11] 4,259,344
[45] Mar. 31, 1981

[54] SULFUR-CONTAINING BENZIMIDAZOLE DERIVATIVES

[75] Inventors: Csaba Gönczi; Dezső Korbonits; Pál Kiss; Endre Pálosi; Gergely Héja; Ida Szvoboda née Kanzel; Judit Cser nee Kun; Maria Szomor nee Wundele; György Körmöczi; Andras Kelemen, all of Budapest, Hungary

[73] Assignee: Chinoin Gyógyszer és Vegyészeti Termékek Gyára R.T., Budapest, Hungary

[21] Appl. No.: 51,247

[22] Filed: Jun. 22, 1979

Related U.S. Application Data

[62] Division of Ser. No. 904,292, May 9, 1978, abandoned.

[30] Foreign Application Priority Data

| May 10, 1977 | [HU] | Hungary | CI1735 |
| May 11, 1977 | [HU] | Hungary | CI1736 |
| May 16, 1977 | [HU] | Hungary | CI1738 |
| Jul. 29, 1977 | [HU] | Hungary | CI1759 |

[51] Int. Cl.³ ............... C07D 235/30; A61K 31/415
[52] U.S. Cl. .................... 424/273 B; 548/306; 260/454
[58] Field of Search ............ 548/306; 424/273 B

[56] References Cited

U.S. PATENT DOCUMENTS 3,965,113  6/1976  Beard et al. .......... 548/306

*Primary Examiner*—John D. Randolph
*Assistant Examiner*—Jane T. Fan
*Attorney, Agent, or Firm*—Karl F. Ross

[57] ABSTRACT

A process for the preparation of anthelmintic compounds of the formula:

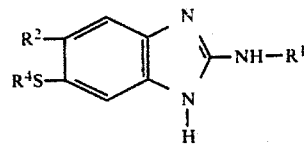

wherein
  $R^1$ is hydrogen or —COOR;
  $R^5$ is $C_1$ to $C_4$ alkyl;
  $R^2$ is halogen, alkyl, trifluoromethyl, alkoxy, aryloxy, or aralkoxy; and
  $R^4$ is hydrogen, alkyl, cycloalkyl; alkenyl, alkynyl or aralkyl;

or pharmaceutically acceptable salts thereof comprises subjecting a bis compound of the formula:

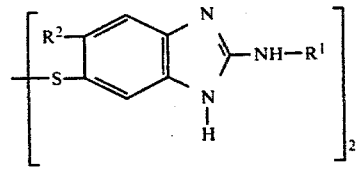

to reduction to cleave the disulfide linkage and where $R^4$ is other then hydrogen, subsequent reaction of the mercapto group. Intermediate compounds and a process for preparing same are also disclosed.

12 Claims, No Drawings

SULFUR-CONTAINING BENZIMIDAZOLE DERIVATIVES

This is a division of application Ser. No. 904,292, filed May 9, 1978.

This invention relates to sulfur-containing benzimidazole derivatives, a process for the preparation thereof and intermediates useful in the production of the same.

Most of the end products of the present invention (Formula I) are new compounds, never described in the literature. The compounds of the formula I possess useful anthelmintic properties and may be used in human and veterinary therapy as anthelmintic agents.

In the formula I

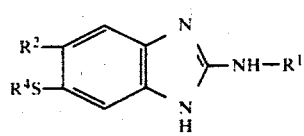

the various symbols have the following definition:
$R^1$ is hydrogen or —COOR$^5$;
$R^5$ is $C_{1-4}$ alkyl;
$R^2$ is hydrogen, halogen, $C_{1-6}$ alkyl, trifluoromethyl or —OR$^3$;
$R^3$ is $C_{1-4}$ alkyl, aryl or aralkyl;
$R^4$ is hydrogen, $C_{1-6}$ alkyl, $C_{3-7}$ cycloalkyl, $C_{3-6}$ alkenyl, $C_{3-6}$ alkynyl, or aryl or aralkyl wherein the aryl ring of the aryl or aralkyl group can be substituted with one or more halogeno, $C_{1-4}$ alkyl, nitro, hydroxy, $C_{1-4}$ alkoxy, $C_{1-4}$ alkylthio, carboxy, or cyano substituent(s) or —S(O)$_n$—R$^8$ in which
$R^8$ is lower alkyl; and
n stands for 0, 1 or 2.

The term lower alkyl-alone or in combinations such as alkoxy, alkylthio etc. relates to straight or branched chain saturated aliphatic hydrocarbon groups having 1-6, preferably 1-4 carbon atoms (e.g. methyl, ethyl, n-propyl, isopropyl, n-butyl, isobutyl, n-amyl etc.). The term "halogeno atom" covers the four halogens i.e. fluorine, chlorine, bromine and iodine. The $C_{3-7}$ cycloalkyl group may be cyclobutyl, cyclopentyl and cyclohexyl preferably. The $C_{3-6}$ alkenyl group may be straight or branched chain and is preferably allyl. The $C_{3-6}$ alkinyl group may be straight or branched chain and represents preferably propinyl. The term "aryl"- used either alone or in combinations such as aralkyl- represents a mono- or bicyclic aromatic ring (e.g. phenyl or naphthyl) which can bear one or more of the conventional substituents of the aromatic rings (e.g. halogeno atom, lower alkyl, lower alkoxy, lower alkylthio, carboxy, nitro, hydroxy, cyano, alkylsulphinyl, alkylsulfonyl, alkylthio etc.).

Some representatives of the compounds of the formula I are disclosed in prior art as anthelmintic agents (e.g. U.S. Pat. Nos. 3,574,845, 3,915,986 and 3,956,499; German Federal Republic Pat. No 2,250,469 and French Pat. No. 2,134,558).

It is known that a certain compound-group of the formula II

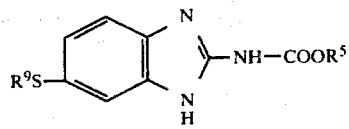

(falling under the scope of the class of compounds of the Formula I, wherein $R^9$ is $C_{1-4}$ alkyl, $C_{3-7}$ cycloalkyl, $C_{36}$ alkenyl, $C_{3-6}$ alkinyl or benzyl) may be prepared by reacting an 1,2-diamino-alkylthio-benzene derivative of the formula III

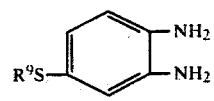

either with an 1,3-bis-(alkoxycarbonyl)-S-alkyl-isothiourea of the formula IV

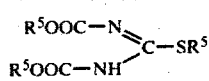

(German Federal Republic Pat. No. 2,363,351—reaction scheme A)

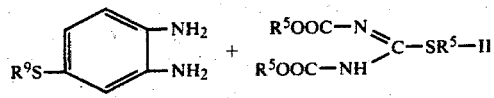

or with a carbalkoxy-cyanamide of the formula V

NC—NH—COOR$^5$     (V)

(U.S. Pat. Nos. 3,915,986 and 3,956,499—reaction scheme B).

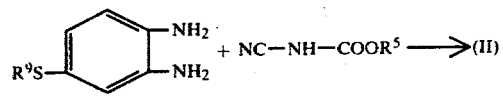

The above procedures suffer from the serious drawback that the benzimidazole carbamate ring system is formed by using 1,2-diamino-4-alkylthio-benzene derivatives of the formula III which can be obtained by means of a complicated multi-step synthesis from relatively expensive starting materials (reaction scheme C) and D)).

Reaction scheme C

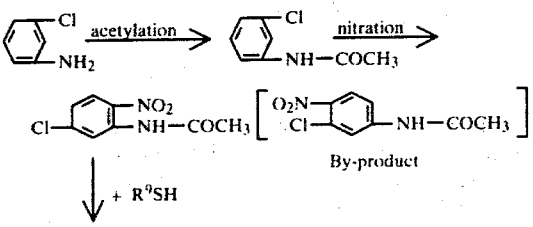

-continued

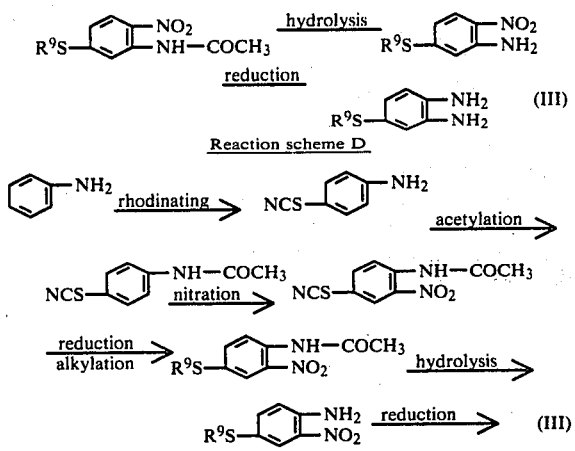

Reaction scheme D

The synthesis route shown in reaction scheme (C) comprises the nitration of m-chloro-acetanilide which gives rise to the formation of two isomeric compounds. Therefore the useful o-nitro-acetamido isomer required for the synthesis is available only with moderate yields [J. Org. Chem. 12, 799 (1947)]. The further step of the reaction needs toxic mercaptanes of very bad odor (U.S. Pat. Nos. 3,915,986 and 3,956,499). This reaction can be generally carried only with low yields [J. Org. Chem. 42, 554 (1977)]. For the reasons stated above the compounds of the formula III are obtained in poor yields.

Reaction scheme (D) provides the desired compounds of the formula III with the aid of a seven-step synthesis by low yields [Ber. 59, 190 (1926); J. Chem. Soc. (1928) 1364].

It has been found that the compounds of the formula I can be prepared by reducing the new benzimidazole-disulfides of the formula VI and if desired subjecting the thiophenol derivative of the formula I thus obtained (R⁴ is hydrogen=Ia)

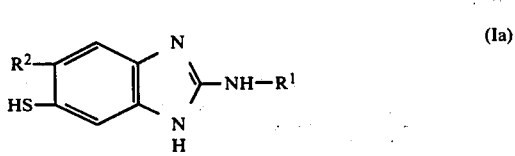

to a selective substitution reaction on the sulfur atom. Thus the compounds of the formula I are available in a simple manner by very good yields.

According to the present invention there is provided a process for the preparation of compounds of the formula I and salts thereof which comprises subjecting a compound of the formula VI

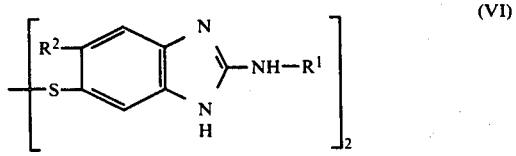

to reduction (wherein $R^1$ and $R^2$ are as stated above) and if desired introducing an $R^4$ group other than hydrogen into the compound of the formula I thus formed (wherein $R^1$ and $R^2$ are as stated above and $R^4$ is hydrogen) and if desired converting a compound of the formula I thus obtained into its salt.

According to a preferred embodiment of our process a compound of the formula VI is reacted with a complex metal hydride such as lithium aluminum hydride, sodiumborohydride-aluminum chloride complex, sodium borohydride or sodium-dihydro-bis-(2-methoxyethoxy)-aluminate in anhydrous medium. As reaction medium preferably organic solvents such as dialkyl ethers, cyclic ethers (e.g. tetrahydrofurane, dioxane), dimethylformamide, dimethylacetamide, hexamethylphosphoric triamide, diethylene-glycol dimethyl ether, lower alcohols etc.) may be used.

When using a sodium borohydride-aluminum chloride complex, the reaction may be preferably carried out in tetrahydrofurane or dioxane. In this case the reaction takes place at room temperature within 2–3 hours.

When using sodium borohydride the reaction may be carried out in addition to the above solvents also in the mixture of water and a lower alkanol in the presence of an alkali hydroxide. The thiophenol derivative of the formula Ia thus formed can either be isolated or directly converted into other compounds of the formula I.

The disulfide bond of the compounds of the formula VI may also be reduced by means of alkali metals. The starting material of the formula VI is suspended in an inert solvent (e.g. toluene, xylene) and admixed with powdered potassium or sodium at room temperature or under warming. 2–4 equivalents of alkali metal are used for 1 equivalent of the compound of the formula VI. If 4 equivalents of alkali are used, the dialkali salt of the compound of the formula Ia is obtained. The reaction mixture is then acidified and the compound of the formula Ia can be isolated if desired. If only 2 equivalents of an acid (e.g. acetic acid) are added to the reaction mixture, the solution of the mono-alkali salt of the compound of the formula Ia is formed which may be converted into other compounds of the formula I directly, without isolation. The said reduction may be preferably accomplished in liquid ammonia at a temperature between −20° C. and −40° C. On evaporating the ammonia solvent the alkali salt of the compounds of the formula Ia is obtained as residue, which may be either isolated or subjected to further reactions.

The compounds of the formula VI may also be reduced with sulfur-containing inorganic reducing agents such as sodium sulfide, sodium sulfite, sodium dithionite, sodium hydrogen sulfite or potassium pyrosulfite. Sodium hydrogen sulfite and sodium dithionite proved to be particularly suitable for this purpose. When using the said reducing agents 2–2.6 moles of alkali hydroxide and 2–2.2 moles of the reducing agent are used for 1 mole of a starting material of the formula VI. Reduction is preferably carried out in an alcoholic solution and/or dimethylformamide containing 10–30% of water. The reaction is accomplished under heating at 50°–80° C., preferably at the boiling point of the reaction mixture. The compounds of the formula Ia formed are either isolated or directly converted into other compounds of the formula I.

As reducing agents organic sulfur compounds may be used as well, (e.g. mercapto-ethanol or amino-iminomethane sulfinic acid). The solution or suspension of the starting material of the formula VI in an organic solvent (e.g. lower alkanol or dimethylformamide) is reacted with 1–3 equivalents of mercapto-ethanol at 20°–80° C. in the presence of a basical catalyst (e.g. triethylamine).

The compounds of the formula Ia thus formed are either directly converted into another compound of the formula I or isolated.

When using amino-imino-methane sulfinic acid as reducing agent, the solution or suspension of the starting material of the formula VI in a mixture of aqueous alkali and alcohol or a dipolar aprotic solvent (in the later case a phase-transmitting catalyst is also added e.g. cetyl-pyridinium bromide and methyl-caprylammonium chloride etc.) is reacted with amino-iminomethanesulfinic acid at 60°–80° C. in an inert atmosphere.

One may also proceed by carrying out reduction with glucose. As solvent or diluent a mixture of water and lower alcohols or dimethylformamide may be used. Reduction takes place at room temperature within 5–10 hours. It is preferred to subject the aqueous alkaline-alcoholic suspension to strong stirring in the presence of a phase-transmitting catalyst. This may significantly shorten the reaction time.

The reduction of the disulfide bond of the starting materials of the formula VI may also be accomplished with metals in acidic medium. As metal preferably zinc, tin, iron or aluminum may be used. One may proceed preferably by using salts of metals of varying valency in which the metal is in a lower oxidation stage [e.g. stannous(II)chloride, titanium(III)chloride] in acidic medium. The suitable pH value may be adjusted by adding a diluted (0.1–2.5 N) inorganic acid such as hydrochloric acid or sulfuric acid. As reaction medium water and/or water-miscible organic solvents (e.g. alkanols, glycols, dimethylformamide, dioxane, diethyleneglycol-dimethylether, tetrahydrofurane, preferably lower alkanols) may be used. The reaction may be preferably carried out at a temperature between 25° C. and 110° C., particularly at the boiling point of the reaction mixture. According to a preferred embodiment of the latter method acetic acid is used which serves both as solvent and for the adjustment of the pH-value.

According to an other method a solution of a compound of the formula VI in the mixture of a mineral acid and alkanol or in dimethylformamide is passed through zinc amalgamated in a Jones-reductor. As mineral acid first of all hydrochloric acid and sulfuric acid may be used. The acid concentration is preferably 0.1–2.5 N. As solvent or diluent water-miscible lower alkanols (e.g. methanol, ethanol or isopropanol) may be used. The above method provides very mild reducing conditions and may be very quickly carried out at room temperature too.

According to a preferred form of realization of the above reducing methods one may work in an inert atmosphere particularly under nitrogen. If the reaction is carried out in heterogeneous system it is expedient to use a phase-transmitting catalyst.

The compounds of the formula Ia thus obtained may be optionally converted into the thio ethers of the formula I—wherein $R^4$ is other than hydrogen—by transforming the said compounds of the formula Ia into a compound of the formula Ib

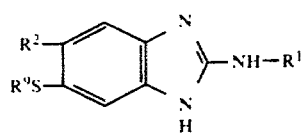

by reacting with a compound of the formula $R^9$-Q; or into a compound of the formula Ic

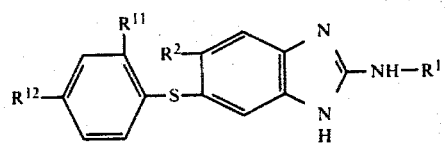

by reacting with a compound of the formula X;

or into a compound of the formula Id

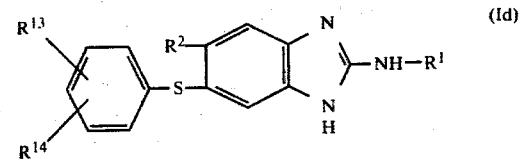

by reacting with a compound of the formula XI;

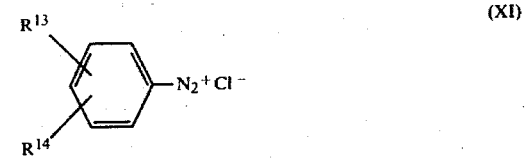

or into a compound of the formula Id, wherein both $R^{13}$ and $R^{14}$ are hydrogen, with chloro-benzene or bromo-benzene, in which formulae $R^9$ is $C_{1-6}$ alkyl; $C_{3-7}$ cycloalkyl, $C_{3-6}$ alkenyl, $C_{3-6}$ alkinyl or aralkyl;

Q is chlorine, bromine or iodine or a group of the formula $R^{10}$—$SO^3$—;

$R^{10}$ is a phenyl group optionally substituted in position 4 by a methyl group;

$R^{11}$ and $R^{12}$ are hydrogen, nitro, cyano, carboxylic group or a group of the formula —$S(O)_n$—$R^8$;

$R^8$ and n are as stated above;

$R^{13}$ and $R^{14}$ are hydrogen, halogen, $C_{1-4}$ alkyl, hydroxy, $C_{1-4}$ alkoxy or alkylthio.

The compound Ia is at first converted into its alkali salt by dissolving or suspending in an organic solvent and adding an equivalent amount of alkali hydroxide (sodium or potassium hydroxide). The solution of this alkali salt—or that of an alkali salt of a compound of the formula Ia directly formed in the course of one of the reducing methods discussed above—is reacted with a compound of the formula $R^9$—Q (wherein $R^9$ and Q are as stated above). The reaction is carried out at a temperature of 10° to 60° C. As solvent or suspending medium water-miscible organic solvents (e.g. methanol, ethanol and/or dimethylformamide, dimethylacetamide, or hexamethylphosphoric triamide) may be used. Thus compounds of the formula Ib are obtained.

The thioethers of the formula Ic may be prepared by reacting a compound of the formula Ia with a compound of the formula X. in this case the compound of the formula Ia is first converted into its alkali salt as described above. The reaction takes place at room temperature within some hours. The reactants are used in equimolar amount. As reaction medium preferably water and/or lower alkanols or dimethylformamide may be used.

The compounds of the formula Id may be prepared by reacting the alkali salt of a compound of the formula Ia—prepared as described above—with a compound of the formula XI. One may proceed preferably by pouring the solution of the diazonium salt of the formula XI to the solution or suspension of an alkali salt of a compound of the formula Ia in a lower alkanol or a mixture of water and a lower alkanol, or water, lower alkanol and dimethylformamide respectively under boiling. The reaction mixture is diluted with water if necessary whereupon the compound of the formula Id is recovered by filtration or extraction. The reaction may be optionnally carried out in the presence of powdered copper.

Compounds of the formula Id—wherein both $R^{13}$ and $R^{14}$ are hydrogen—may also be prepared by reacting the alkali salt of a compound of the formula Ia with chloro-benzene or bromo-benzene at 100°–200° C. in the presence of 0.1–2.5 equivalents of a heavy metal salt [e.g. cuprous(I)- or cupric(II)-salt such as cupric(II)-chloride or cupric(II)-bromide].

The conversion of the compounds of the formula Ia into thioethers of the formula I ($R^4$ is other than hydrogen) is carried out in inert atmosphere preferably under nitrogen. Reactions in heterogenous system are expediently carried out in the presence of a phase transmitting catalyst in order to shorten reaction time and to increase the yield. For this purpose both phosphonium and ammonium type phase transmittants may be readily applied which are generally used in chemistry.

According to a further feature of our invention there are provided new compounds of the formula I and salts thereof (wherein $R^1$, $R^2$ and $R^4$ have the same meaning as stated above with the proviso that $R^2$ is other than hydrogen).

Preferable sub-class of the compounds of the formula I are those derivatives wherein $R^1$ is —COOR$^5$; $R^5$ is lower alkyl, preferably methyl; $R^4$ is lower alkyl, preferably methyl, ethyl or n-propyl; allyl, propinyl, benzyl or cyclohexyl and $R^2$ is halogen preferably chlorine, bromine or fluorine; lower alkoxy, preferably methoxy; lower alkyl, preferably methyl; or trifluoromethyl.

Particularly preferable representatives of the compounds of the formula I are the following derivatives,
5(6)-n-propylthio-6(5)-fluoro-benzimidazolyl-2-methyl-carbamate;
5(6)-n-propylthio-6(5)-chloro-benzimidazolyl-2-methyl-carbamate;
5(6)-benzylthio-6(5)-chloro-benzimidazolyl-2-methyl-carbamate;
5(6)-allylthio-6(5)-chloro-benzimidazolyl-2-methyl-carbamate;
5(6)-propynyl-6(5)-chloro-benzimidazolyl-2-methyl-carbamate;
5(6)-ethylthio-6(5)-chloro-benzimidazolyl-2-methyl-carbamate;
5(6)-cyclohexylthio-6(5)-chloro-benzimidazolyl-2-methyl-carbamate;
5(6)-n-propylthio-6(5)-bromo-benzimidazolyl-2-methyl-carbamate;
5(6)-n-propylthio-6(5)-methyl-benzimidazolyl-2-methyl-carbamate;
5(6)-n-propylthio-6(5)-methoxy-benzimidazolyl-2-methyl-carbamate;
5(6)-n-propylthio-6(5)-n-butyl-benzimidazolyl-2-methyl-carbamate;
5(6)-n-propylthio-6(5)-trifluoromethyl-benzimidazolyl-2-methyl-carbamate.

According to a still further feature of the present invention there are provided anthelmintic compositions comprising an active ingredient a compound of the formula I (wherein $R^1$, $R^2$ and $R^4$ are as stated above with the proviso that $R^2$ is other than hydrogen) or a salt thereof in admixture with suitable inert non-toxic solid or liquid carriers or diluents.

The compounds of the formula I possess useful anthelmintic properties and may be used in human and veterinary therapy as anthelmintic agent. The new compounds of the formula I and salts thereof are formulated with non-toxical animal veterinary or feed carrier to give a usual anthelmintic composition. The carrier may be a standard animal feed composition based on a feed carrier or an orally ingestible container for the active ingredient for example a hard or soft gelatine capsule. It may also be a pharmaceutically acceptable diluent or excipient of the kind normally used in the production of medicaments (e.g. starch, lactose, sucrose, calcium phosphate, gelatine, talcum, magnesium stearate, dextrin, agar etc.). As liquid carrier e.g. peanut oil, olive oil, sesame oil and water may be used.

A wide variety of pharmaceutical and veterinary forms can be employed. Thus if a solid carrier is used the composition can be tableted, placed in a hard gelatine capsule, compounded in a salt block, as a powder for drench or gavage use, whole feed or other conventional formulations. The compositions are often finished in forms suitable for oral administration (e.g. solution, emulsion, suspension in water or an edible oil). The administration may also be carried out with such forms as bolus, tablet, drench, top dressing etc.

The anthelmintic compositions of the present invention are made by conventional methods by admixing the active ingredient or a salt thereof with suitable inert solid or liquid carriers or diluents.

The salts of the compounds of the formula I are pharmaceutically acceptable salts.

The dosage of the active ingredient may vary between wide ranges depending on various factors (e.g. seriousness of the infection, condition and weight of the host etc.) and may be generally between about 0.5 mg/kg and 150 mg/kg, preferably 2–20 mg/kg of body weight/dose. The daily active ingredient content may be administered at once or in more doses.

The starting materials of the formula VI and salts thereof are new compounds. According to a further feature of the present invention, there are provided new compounds of the formula VI and salts thereof and a process for their preparation (wherein $R^1$, $R^5$, $R^2$ and $R^3$ have the same meaning as stated above). The compounds of the formula VI are useful as intermediates in the preparation of the anthelmintic compounds of the formula I while on the other hand they possess themselves fungicidal and anthelmintic properties and can be used in agriculture as fungicides and in pharmacy as anthelmintics.

The preferred class of the compounds of the formula VI are those derivatives in which $R^1$ is hydrogen or methoxycarbonylamino and $R^2$ is hydrogen, chlorine, bromine, fluorine, trifluoromethyl, methyl, butyl or —OR$^3$ wherein $R^3$ is methyl, phenyl or benzyl.

Particularly useful intermediates of the formula VI are the following derivatives:

bis-(2-amino-benzimidazole-5-yl)-disulfide;
bis-(2-amino-6-methyl-benzimidazole-5-yl)-disulfide;
bis-(2-amino-6-butyl-benzimidazole-5-yl)-disulfide;
bis-(2-amino-6-bromo-benzimidazole-5-yl)-disulfide;
bis-(2-amino-6-chloro-benzimidazol-5-yl)-disulfide;
bis-(2-amino-6-fluoro-benzimidazole-5-yl)-disulfide;
bis-(2-amino-6-trifluoromethyl-benzimidazole-5-yl)-disulfide;
bis-(2-amino-6-methoxy-benzimidazole-5-yl)-disulfide;
bis-(2-amino-6-phenyloxy-benzimidazole-5-yl)-disulfide;
bis-(2-amino-6-benzyloxy-benzimidazole-5-yl)-disulfide;
bis-(2-methoxycarbonylamino-benzimidazole-5-yl)-disulfide;
bis-(2-methoxycarbonylamino-6-methyl-benzimidazole-5-yl)-disulfide;
bis-(2-methoxycarbonylamino-6-butyl-benzimidazole-5-yl)-disulfide;
bis-(2-methoxycarbonylamino-6-bromo-benzimidazole-5-yl)-disulfide;
bis-(2-methoxycarbonylamino-6-chloro-benzimidazole-5-yl)-disulfide;
bis-(2-methoxycarbonylamino-6-fluoro-benzimidazole-5-yl)-disulfide;
bis-(2-methoxycarbonylamino-6-trifluoromethyl-benzimidazole-5-yl)-disulfide;
bis-(2-methoxycarbonylamino-6-methoxy-benzimidazole-5-yl)-disulfide;
bis-(2-methoxycarbonylamino-6-phenoxy-benzimidazole-5-yl)-disulfide;
bis-(2-methoxycarbonylamino-6-benzyloxy-benzimidazole-5-yl)-disulfide;

The compounds of the formula VI may be prepared as follows:

(a) for the preparation of compounds of the formula VI, wherein $R^1$ is hydrogen, reacting a compound of the formula VII

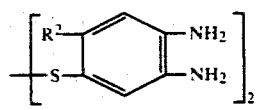
(VII)

(wherein $R^2$ has the same meaning as stated above) with cyanamide or bromo cyane; or (b) for the preparation of compounds of the formula VI, wherein $R^1$ is a group of the formula $-COOR^5$ and $R^5$ is as stated above, reacting a compound of the formula VII with a compound of the formula XII $$R^5OOCN=C-NH-COOR^5$$
$$|$$
$$SR^5$$
(XII)

or

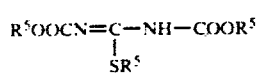
(XIII)

(in which formulae $R^5$ is as stated above) or reacting a compound of the formula VI, wherein $R^1$ is hydrogen, with an agent suitable for the introduction of the group of the formula $-COOR^5$, such as a compound of the formula XIV

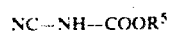
(XIV)

or XV $$(R^5O)_2CO$$
(XV)

(wherein $R^5$ is as stated above and X is halogen) and if desired converting a compound of the formula V, thus obtained into its salt or setting free the same from its salt.

According to one embodiment of method (a) a compound of the formula VII is reacted with cyanamide. The reaction is accomplished in the presence of a mineral acid (e.g. hydrochloric acid, sulfuric acid, phosphoric acid) in aqueous medium. Thereafter the reaction mixture is treated with an inorganic base (e.g. sodium or potassium hydroxide) or an alkali carbonate (e.g. sodium or potassium carbonate) and the precipitated bis-(2-aminobenzimidazolyl)-disulfide of the formula VIa

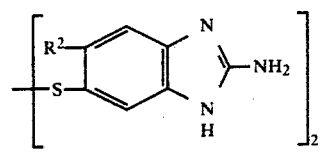
(VIa)

is isolated.

According to an other embodiment of method (a) a compound of the formula VII is reacted with bromo cyane in a lower alkanol (e.g. methanol, ethanol, propanol, isopropanol, preferably in ethanol) at a temperature between 0° C. and 40° C., preferably at 20° C. The reaction mixture is treated with an alkali (e.g. sodium or potassium hydroxide) or an alkali carbonate (e.g.. sodium or potassium carbonate) to give a compound of the formula VIa.

According to an embodiment of method (b) of our process a compound of the formula VII is reacted with an isothiourea derivative of the formula XII. The process is preferably carried out by heating the components in a protic solvent in the presence of an acid. As reaction medium water, or organic solvents or a mixture of water and an organic solvent (e.g. water-ethanol mixture) may be used. The reaction is preferably accomplished at a pH value of 3-6, particularly at an interval of 3.5-5. The pH is adjusted with an inorganic acid (e.g. hydrochloric acid, sulfuric acid, phosphoric acid) or an organic acid, e.g. formic acid, acetic acid, propionic acid etc. preferably acetic acid. The reaction temperature is preferably 50°-100° C. and one may work advantageously at the boiling point of the reaction mixture. Thus compounds of the formula VIb

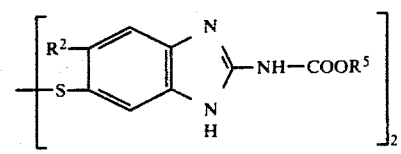
(VIb)

are obtained.

According to an other embodiment of method (b) a compound of the formula VII is reacted with a carbalkoxy-cyanamide of the formula XIII in a water-miscible organic solvent (e.g. methanol, ethanol, acetone, dioxane, pyridine) or a mixture of water and an organic solvent. The reaction may be accomplished preferably at a temperature between 20° C. and the boiling point of the reaction mixture. Thus, compounds of the formula VIb are obtained.

A compound of the formula VIa may be converted into the corresponding compound of the formula VIb by reacting with an agent capable for the introduction of a carbalkoxy group. Reaction is carried out preferably in a basical organic solvent (e.g. pyridine) at a temperature of 0°-100° C. As agent capable for the introduction of a carbalkoxy group agents generally used for this purpose (e.g. alkyl halogeno formiates of the formula XIV) may be used.

The compounds of the formula VIa may also be transformed into the corresponding compounds of the formula VIb by reacting with a dialkyl carbonate of the formula XV in the presence of an equimolar amount of an alkali alcoholate. As solvent preferably an alkanol may be used. One may proceed preferably by using as reaction medium an alcohol which corresponds to the $R^5$ alkyl group of the alkali alcoholate. The reaction temperature amounts to 20°-120° C., preferably the boiling point of the alcohol solvent used.

It is evident for one skilled in the art that the compounds appearing in the examples may be designated in two manners depending on the fact whether the numbering is started from the N-atom or the NH group. Thus bis-(2-methoxycarbonylamino-benzimidazole-5-yl)-disulfide can also be named as bis-(2-methoxycarbonylaminobenzimidazole-6-yl)-disulfide.

According to a further feature of the present invention there are provided compounds of the formula VII and salts thereof and a process for the preparation of the same. The compounds of the formula VII are useful on the one hand as intermediates in the preparation of anthelmintic agents of the formula I while on the other they possess valuable fungicidal and anthelmintic properties and may be used as fungicides in agriculture and anthelmintics in pharmacy.

All of the compounds of the formula VII are new except the derivative in which $R^2$ is hydrogen. In prior art a very complicated and circumstantial seven-step synthesis is disclosed for the preparation of this compound in which aniline is rhodinated, the amino group is protected by introducing an acetyl group, the product is subjected to nitration and hydrolysis, whereupon the product obtained is converted into a disulfide, which is then cleaved into 2-amino-4-mercapto-aniline and finally a disulfide is formed [Ber. 59, 190 (1926); J. Chem. Soc. 1928, 1364; Pharmazie 3, 151 (1948); Arzneimittelforschung 2, 455 (1952)]. In view of the complicated steps and the low yield this process is unsuitable for industrial scale production. The compound of the formula VII, wherein $R^2$ is hydrogen, was only known as a laboratory product of theoretical interest.

It has been found that the compounds of the formula VII are valuable intermediates in the preparation of biologically active derivatives by further reactions of the active amino groups. Thus they are suitable for the preparation of various heterocyclic compounds, e.g. dibenzimidazolyldisulfide derivatives. The following preparation of the compounds of the formula VII can be readily carried out on industrial scale. Practically no by-products are formed.

The compounds of the formula VII may be prepared by heating a compound of the formula XVI.

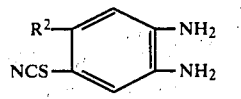
(XVI)

The reaction may be carried out preferably by heating the starting material of the formula XVI in a suitable solvent in the presence of a catalyst.

As solvent water or lower alkanols (e.g. methanol, ethanol, propanol) or a mixture of water and the above alkanols may be used. The catalyst may be an inorganic base (preferably sodium hydroxide, potassium hydroxide, an alkali carbonate (e.g. sodium carbonate, potassium carbonate) or, preferably, ammonium hydroxide.

One may proceed particularly preferably by heating a compound of the formula XVI with a 3.5% aqueous ammonium hydroxide solution. The reaction temperature is preferably 20°-100° C., advantageously 80° C. The reaction takes place within 1-5 hours, preferably 3 hours.

According to an other embodiment of this process a compound of the formula XVI is heated in the mixture of a lower alkanoic acid (e.g. acetic acid) and a tertiary amine (e.g. triethylamine, dimethylaniline, pyridine).

Particularly preferable class of compounds are those derivatives of the formula VII wherein $R^2$ is methyl, butyl, chlorine, bromine, fluorine, trifluoromethyl or —$OR^3$ and $R^3$ is methyl, benzyl or phenyl.

Particularly preferred representatives of the compounds of the formula VII are the following compounds:

2,2'-dimethyl-4,4',5,5'-tetraamino-diphenyl-disulfide;
2,2'-dibutyl-4,4',5,5'-tetraamino-diphenyl-disulfide;
2,2'-dibromo-4,4',5,5'-tetraamino-diphenyl-disulfide;
2,2'-dichloro-4,4',5,5'-tetraamino-diphenyl-disulfide;
2,2'-difluoro-4,4',5,5'-tetraamino-diphenyl-disulfide;
2,2'-di-(trifluoromethyl)-4,4',5,5'-tetraamino-diphenyl-disulfide;
2,2'-dimethoxy-4,4',5,5'-tetraamino-diphenyl-disulfide;
2,2'-diphenoxy-4,4'-5,5'-tetraamino-diphenyl-disulfide;
2,2'-di-(benzyloxy)-4,4',5,5'-tetraamino-diphenyl-disulfide.

According to a still further aspect of our invention there are provided compounds of the formula XVII

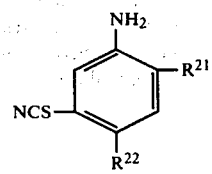
(XVII)

salts thereof and a process for the preparation of the same.

In the compounds of the formula XVII $R^{21}$ stands for hydrogen or amino; and if $R^{21}$ is hydrogen, then $R^{22}$ is amino and if $R^{21}$ represents amino, then $R^{22}$ stands for hydrogen, halogen, trifluoromethyl, lower alkyl, lower alkoxy, aryloxy or aralkoxy- The compounds of the formula XVII and salts thereof are prepared by reacting a compound of the formula XVIII

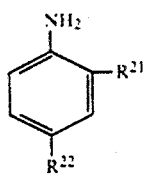
(XVIII)

(wherein $R^{21}$ and $R^{22}$ are as stated above) with an agent capable of introducing a thiocyanato (SCN) group in anhydrous medium and if desired converting a compound of the formula XVII into its salt of setting free the same from its salt.

The compounds of the formula XVII are useful intermediates which may be used in the preparation of biologically active compounds, particularly pharmaceuticals and products for application in agriculture such as pesticides, e.g. fungicides.

One of the compounds of the formula XVII-the 1,2-diamino-4-thiocyanato-benzene-has been described as intermediate without disclosing its physical constants (Hungarian laid open patent application Serial No. SI-1367). According to the known process 1-amino-2-nitro-4-thiocyanato-benzene (J. Chem. Soc. 1928, 1364—a compound which is available with difficulty on an industrial scale—is reduced with stannous (II)chloride at −40° C. (Reaction scheme E)

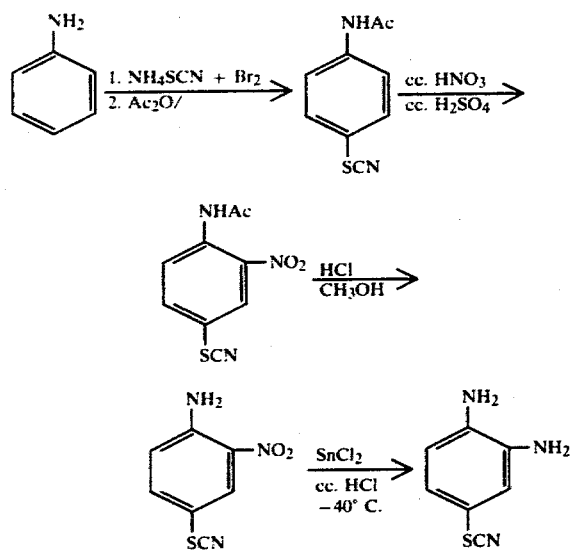

It is known [J. Gen. Chem. (USSR), 3, 183 (1933); C.A. 28, 1677 (1934) that 1,3-diamino-benzene may be rhodinated with the aid of N,N'-dichloro-urea and ammonium rhodanide in aqueous acetic acid. The authors stated however that this method does not lead to the desired result when diamino-benzene derivatives sensible against oxidation (such as p-phenylene-diamine) are used. A recently published summarizing monograph about rhodinating was silent in teaching the rhodination of such diamino-benzene derivatives [Die Pharmazie 32, 195 (1977)].

It has been found surprisingly that the diamino-thiocyanato benzene derivatives of the formula XVII may be prepared by excellent yields from the compounds of the formula XVIII by direct rhodination in moderately acidic anhydrous medium.

According to the process of the present invention as rhodinaing agent preferably compounds of the formula XIX $$R^4-SCN \quad (XIX)$$

may be used (wherein $R^4$ is a metal atom, preferably an alkali metal atom, alkaline earth metal atom or a heavy metal atom or an ammonium ion) in the presence or in the absence of an oxidizing agent—depending on the definition of $R^4$. These rhodinating agents provide under the reaction conditions used the desired compounds of the formula XVII in a simple manner, by excellent yields and in high purity.

One may proceed preferably by preparing in advance the active rhodinating agent and adding the same to the solution of the starting material of the formula XVIII. The active rhodinating agent may also be prepared by reacting a compound of the formula XIX with an oxidizing agent. In this reaction both inorganic and organic oxidizing agents may be used. The suitable oxidizing agents include organic N-halogeno compounds, such as Chloramine-T, N-bromo-succinimide, N,N'-dichloro-urea; peroxides e.g. hydrogen peroxide; alkali hypochlorites, alkali bromates, alkali iodates; ions of heavy metals of suitable oxidation grade e.g. ions of lead, magnanese and chromium; silver oxide and elemental halogens such as chlorine and bromine can also be used.

One may also proceed by adding the above oxidizing agent at a suitable rate to the solution of the compounds of the formulae XVIII and XIX. In the case of rhodanides of heavy metals however this embodiment of the process is less preferable.

According to a paeticularly preferable embodiment of our process the oxidizing agent or a solution thereof is added at a suitable rate to the solution of a compound of the formula XVIII and a rhodanide of the Formula XIX wherein $R^4$ is ammonium, sodium or potassium ion, preferably ammonium ion. One may use preferably an elemental halogen, particularly bromine or chlorine.

As reaction medium organic solvents may be used in which the components are readily soluble such as dipolar aprotic solvents (e.g. dimethylformamide, dimethylsulfoxide, hexamethylphosphoric triamide, lower fatty acids, esters of alcohols formed acetic acid or formic acid and alkanols having 1–4 carbon atoms). It is preferred to use methanol or ethanol in which most organic rhodanides are easily soluble. Methanol proved to give the best results. In the case of the preparation of compounds of the formula XVII wherein $R^{21}$ is amino and $R^{22}$ is alkyl, alkoxy, aryloxy or aralkoxy, the reaction is carried out under the addition of an acid. For this purpose organic acids may be very advantageously used which act also as solvent (e.g. acetic acid or formic acid). One may proceed particularly preferably by using methanol or ethanol as solvent and adding 0–2 moles of acetic acid—related to the diamino-benzene derivative of the formula XVIII—to the reaction mixture.

The reaction temperature depends on the solvent and the reactants used and is from about −20° C. to about +200° C.

The process may be particularly advantageously accomplished by reacting a compound of the formula XVIII in a mixture of methanol and acetic acid at a temperature between −10° C. and +25° C. with a rhodinating agent formed from ammonium rhodanide and elementary bromine or chlorine.

The above novel process opens a new way in the synthesis of sulfur-containing diamino-benzene derivatives. The process is very simple, the starting materials are inexpensive and easily available in large quantities and the desired diamino-thiocyanato-benzene derivatives are obtained in one step with excellent yields.

It is evident for one skilled in the art that the numbering of the substituents may be started from either amino group. Thus 1,2-diamino-4-chloro-5-thiocyanato-benzene may be designated as 1,2-diamino-4-thiocyanato-5-chlorobenzene as well.

The compounds of the formula XVII are new and also belong to the scope of our invention, with the proviso that if $R^{21}$ is amino then $R^{22}$ is other than hydrogen.

Preferred representatives of the compounds of the formula XVII are the following derivatives:
1,2-diamino-4-methyl-5-thiocyanato-benzene;
1,4-diamino-2-thiocyanato-benzene;
1,2-diamino-4-chloro-5-thiocyanato-benzene;
1,2-diamino-4-bromo-5-thiocyanato-benzene;
1,2-diamino-4-fluoro-5-thiocyanato-benzene;
1,2-diamino-4-trifluoro-ethyl-5-thiocyanato-benzene
1,2-diamino-4-methoxy-5-thiocyanato-benzene;
1,2-diamino-4-phenoxy-5-thiocyanato-benzene;
1,2-diamino-4-benzyloxy-5-thiocyanato-benzene;
1,2-diamino-4-n-butyl-5-thiocyanato-benzene.

The compounds of the formula I and salts thereof (wherein $R^1$, $R^2$, $R^3$, and $R^4$ and $R^5$ are as stated above) may be thus prepared from the diamino-benzene derivatives of the formula XVIII by the following reaction series: reacting a compound of the formula XVIII (wherein $R^{21}$ is amino and $R^{22}$ stands for hydrogen, halogen, trifluoromethyl, lower alkyl, lower alkoxy, aryloxy or aralkoxy) with an agent capable of introducing a thiocyanato-group (SCN); thereafter heating the compund of the formula XVI thus formed and reacting the compound of the formula VII then formed with cyanamide, bromine cyanide or a compound of the formula XII or XIII and if desired reacting a compound of the formula VI thus formed (wherein $R^1$ is hydrogen) with a compound of the formula XIV or XV (wherein $R^5$ is as stated above and X is halogen) to give a compound of the formula VI wherein $R^2$ is as stated above and $R^1$ is a group of the formula —$COOR^5$, in which formula $R^5$ is as stated above); and thereafter subjecting a compound of the Formula VI to reduction and if desired introducing an $R^4$ group being other than hydrogen into a compound of the formula I thus formed (wherein $R^4$ is hydrogen) and if desired converting a compound of the formula I thus obtained into its salt.

According to a particularly preferred aspect of the present invention there is provided a new process for the preparation of 5(6)-n-propylthio-benzimidazolyl-2-methylcarbamate (a well-known anthelmintic agent—a compound of the Formula I wherein $R^1$ is methoxycarbonyl; $R^2$ is hydrogen and $R^4$ is n-propyl) which comprises reacting o-phenylene-diamino with an agent of introducing a thiocyanato group (SCN); heating the compound of the formula (XVI) thus obtained (wherein $R^2$ is hydrogen); reacting the compound of the formula VII thus obtained (wherein $R^2$ is hydrogen) with cyanamide, bromocyane or a compound of the formula XII or XIII (wherein $R^5$ is methyl)—whereby if cyanamide or bromine cyanide is used, the product thus obtained is reacted with a compound of the formula XIV or XV (wherein $R^5$ is methyl); reducing the compound of the formula VI thus obtained (wherein $R^2$ is hydrogen; $R^1$ is —$COOR^5$ and $R^5$ is methyl) and reacting the compound of the formula I thus obtained (in which $R^2$ and $R^4$ are hydrogen; $R^1$ is —$COOR^5$ and $R^5$ is hydrogen) with a propylating agent.

Further details of the present invention are to be found in the Examples without limiting the scope of our invention to the Examples.

EXAMPLE 1

10.8 g of o-phenylene diamine and 18.2 g of ammonium rhodanide are dissolved in a mixture of 80 ml of methyl alcohol and 10 ml of acetic acid and to the mixture cooled at a temperature of 10° C. a solution of 6.5 ml of bromine in 20 ml of methyl alcohol is added while stirring in 30–60 minutes and the temperature is maintained at 10° C. while stirring until the reaction is finished (5 to 30 minutes).

The final point of the reaction is determined by thin-layer chromatographic analysis (Layer: Polyram Sil. G., Macherey Nagel Co.: Development with: benzene-ethylacetatemethyl alcoholic ammonium solution 8:1:1. Developer:Iodine).

The reaction finished the mixture is poured into water and the acid is neutralized by adding a 20% ammonium hydroxide solution, pH value 7–7.5. The precipitated crystalline 1,2-diamino-4-thio-cyanato-benzene is filtered. Weight: 13.2 g (yield 80%). Melting point 123° C. (recrystallized from benzene).

EXAMPLE 2

10.8 g of phenylene diamine and 50 g of potassium rhodanide are dissolved in 1100 ml of methyl alcohol and to the solution at a temperature of 10° C. a solution of 7.0 ml of bromine in 30 ml of methyl alcohol is added while stirring vigorously in 30–60 minutes. The final point of the reaction is determined by the method set forth in Example 1. After pouring the mixture into water and adjusting the pH value, the product is isolated by extraction with chloroform. After drying and evaporating the solvent 13.5 g of 1,2-diamino-4-thiocyanato-benzene are obtained. Mp. 123° C. (from benzene).

EXAMPLE 3

15.9 g of bromine are added dropwise while stirring into a solution of 20 g of potassium rhodanide in 100 ml of methyl alcohol at a temperature of −10° C. The obtained yellowish birhodane solution is added to a solution of 10.8 g of o-phenylene diamine in 40 ml of a mixture from acetic acid-methyl alcohol 1:1, while stirring at a temperature of 5°–10° C. Processing the reaction mixture as set forth in Example 1 the 1,2-diamino-4-thiocyanatobenzene is obtained, melting at 123° C.

EXAMPLE 4

To a solution of 14.2 g of 4(5)-chloro-o-phenylene diamine and 38 g of ammonium rhodanide in 120 ml of methyl alcohol 5 ml of acetic acid are added, whereafter a solution of 7.2 ml of bromine in 20 ml of methyl alcohol is added at a temperature of 15°–17° C. in 30–60 minutes.

The mixture is diluted with water and after adjusting the pH value to 8, 1,2-diamino-4-chloro-5-thiocyanato-benzene is obtained, melting at 108°–110° C.

EXAMPLE 5

To a solution of 13.8 g of 4(5)-methoxy-o-phenylene diamine and 38 g of ammonium rhodanide in 80 ml of methyl alcohol and 15 ml of acetic acid a solution of 6.5 ml of bromine in 20 ml of methyl alcohol is added dropwise within 40–60 minutes at a temperature of 5°–10° C. Processing the reaction mixture as set forth in Example 1 the 1,2-diamino-4-methoxy-5-thiocyanato-benzene is obtained. Mp.: 112°–114° C.

EXAMPLE 6

21.4 g of 4(5)-benzyloxy-o-phenylene diamine and 50 g of potassium rhodanide are dissolved in a mixture of 100 ml of methyl alcohol and 20 ml of acetic acid and to the solution obtained a solution of 6.5 ml of bromine in 30 ml of methyl alcohol is added at a temperature of 5°–10° C. in 30–60 minutes. Processing the mixture as set forth in Example 1 the 1,2-diamino-3-benzyloxy-4-thiocyanato-benzene is obtained.

EXAMPLE 7

To a solution of 10.8 g. of p-phenylene-diamine and 38 g of ammonium rhodanide in 100 ml of methyl alcohol and 15 ml of acetic acid a solution of 6.5 ml of bromine in 25 ml of methyl alcohol is added while stirring at a temperature of 8°–10° C. Processing the reaction mixture as set forth in Example 1 the 1,4-diamino-2-thiocyanato-benzene is obtained.

EXAMPLE 8

In an analogous manner to the process described in Example 1 to 3, the following compounds are prepared:

1,2-diamino-4-methyl-5-thiocyanato-benzene, mp.: 117° C.,
1,2-diamino-4-chloro-5-thiocyanato-benzene; mp.: 108°–110° C.;
1,2-diamino-4-bromo-5-thiocyanato-benzene, mp.: 99°–100° C.;
1,2-diamino-4-fluoro-5-thiocyanato-benzene, mp.: 104°–106° C.;
1,2-diamino-4-trifluoromethyl-5-thiocyanato-benzene, mp.: 154°–156° C.;
1,2-diamino-4-n-butyl-5-thiocyanato-benzene, mp.: 109°–110° C.;

EXAMPLE 9

22.0 g of 1,2-diamino-4-thiocyanato-benzene are dissolved in 100 ml. of methyl alcohol and to the solution 100 ml. of a 25% ammonium hydroxide solution and 1000 ml of water are added. The mixture is kept at a temperature of 80°–85° C. for 3–4 hours. The final point of the reaction is determined by thin layer chromatographic analysis. (Layer: Macherey-Nagel Polygram Sil. G. Developtment with: benzene-ethylacetate—a 10% alcoholic ammonia solution 8:1:1. Developer: Iodine Rf 0.48).

When reaction is complete, the mixture is cooled, let to stand overnight in a refrigerator and the precipitated product is filtered, washed with water and dried. 16.1 g of 3,3',4,4'-tetraamino-diphenyl-disulfide are obtained (Yield 87%), melting point: 161°–162° C.

EXAMPLE 10

16.5 g of 1,2-diamino-4-thiocyanato-benzene are dissolved in 20 ml of acetic acid and after the addition of 4 g of pyridine catalyst the reaction mixture is boiled. The final point of the reaction is determined by thin layer chromatographic analysis (see Example 1). The mixture is poured on 200 g of ice-water, and is then made alkaline by adding a 4 N sodium hydroxide solution (pH value 7.5–8).

After standing for a half hour the product is filtered, washed with water and dried. 11.1 g (yield 81%) of 3,3'4,4'-tetraamino-diphenyl-disulfide are obtained. Mp. 161°–162° C.

EXAMPLE 11

One proceeds in the same way as in Examples 9 or 10, with the difference, that instead of 1,2-diamino-4-thiocyanatobenzene an equivalent amount of a compound of the formula XVI is used, wherein $R^2$ represents a methyl-, butyl-, bromine-, chlorine-, fluorine-, trifluoromethyl-, methoxy-, phenoxy- or benzyloxy group.

By this way the following compounds of the formula VII are prepared:

2,2'-dimethyl-4,4',5,5'-tetraamino-diphenyl-disulfide, mp.: 174°–175° C.;
2,2'-dibutyl-4,4=,5,5'-tetraamino-diphenyl-disulfide, mp.: 205°–207° C.;
2,2'-dibromo-4,4'-5,5'-tetraamino-diphenyl-disulfide, mp.: 179°–180° C.;
2,2'-dichloro-4,4',5,5'-tetraamino-diphenyl-disulfide; mp.: 182°–183° C.;
2,2'-difluoro-4,4',5,5'-tetraamino-diphenyl-disulfide, mp.: 172°–173° C.;
2,2'-di(trifluoromethyl)-4,4',5,5'-tetraamino-diphenyl-disulfide, mp: 194°–196° C.;
2,2'-dimethoxy-4,4',5,5'-tetraamino-diphenyl-disulfide, mp.: 190°–192° C.;
2,2'-diphenoxy-4,4',5,5'-tetraamino-diphenyl-disulfide,
2,2'-di-benzyloxy-4,4',5,5'-tetraamino-diphenyl-disulfide.

EXAMPLE 12

2.78 g of 3,3',4,4'-tetraamino-diphenyl-disulfide and 6.0 g of S-methyl-isothiourea-diurethane are dissolved in 100 ml of a 50 vol% alcohol and 1 ml of acetic acid is added, the mixture is boiled until the methyl mercaptane evolution ceases (about 3 hours), whereafter the precipitated bis-(2-methoxycarbonyl-benzimidazole-5-yl)disulfide is filtered, washed and dried. 4.2 g of the product are obtained (95%), melting point 328° C. (decomposition).

EXAMPLE 13

8.8 g of sodium hydroxide are dissolved in 50 ml of wter and 4.2 g of cyanamide are added. The mixture is cooled to 10° C. and 9.4 g of chloro-formic acid methyl ester are added dropwise in 30–45 minutes. The mixture is stirred for a further half hour, then added to a solution of 13.9 g of 3,3',4,4'-tetraamino-diphenyl-disulfide in 200 ml of a 75 vol% alcohol. The reaction mixture is boiled and the pH value is maintained between 3–4 by adding some concentrated hydrochloric acid at intervals. After boiling for 90 minutes the mixture is cooled to room temperature and the precipitated product is isolated by filtration. 19.0 g of the bis(2-methoxycarbonylamino-benzimidazole-5-yl)disulfide are obtained. Melting point: 325° C. (decomposition).

EXAMPLES 14 TO 22

One proceeds according to the process of the Examples 12 to 13 by using the following o-phenylene diamine derivatives:

2,2'-dimethyl-4,4',5,5'-tetraamino-diphenyl-disulfide,
2,2'-dibutyl-4,4',5,5'-tetraamino-diphenyl-disulfide,
2,2'-dibromo-4,4',5,5'-tetraamino-diphenyl-disulfide, 2,2'-dichloro-4,4',5,5'-tetraamino-diphenyl-disulfide,
2,2'-difluoro-4,4',5,5'-tetraamino-diphenyl-disulfide,
2,2'-di(trifluoromethyl)-4,4'5,5'-tetraamino-diphenyl-disulfide,
2,2'-dimethoxy-4,4',5,5'-tetraamino-diphenyl-disulfide,
2,2'-diphenoxy-4,4'-5,5'-tetraamino-diphenyl-disulfide,
2,2'-dibenzyloxy-4,4',5,5'-tetraamino-diphenyl-disulfide.

In this way the following products were obtained:

bis(2-methoxycarbonyl-amino-6-methyl-benzimidazole-5-yl)-disulfide, mp.: 305°–10° C.;
bis(2-methoxycarbonyl-amino-6-butyl-benzimidazole-5-yl)-disulfide, mp. 295°–8° C.
bis(2-methoxycarbonyl-amino-6-bromo-benzimidazole-5-yl)-disulfide, mp.: 310° C. (d).
bis(2-methoxycarbonyl-amino-6-chloro-benzimidazole-5-yl)-disulfide, mp. 305°–310° C. (d).
bis(2-methoxycarbonyl-amino-6-fluoro-benzimidazole-5-yl)-disulfide, mp. 285°–288° C.
bis(2-methoxycarbonyl-amino-6-trifluoromethyl-benzimidazole-5-yl)-disulfide, mp: above 340.° C.
bis(2-methoxycarbonyl-amino-6-methoxy-benzimidazole-5-yl)-disulfide, Mp.: 297°–300° C. (b).
bis(2-methoxycarbonyl-amino-6-phenoxy-benzimidazole-5-yl)-disulfide
bis(2-methoxycarbonyl-amino-6-benzyloxy-benzimidazole-5-yl)-disulfide.

EXAMPLE 23

2.78 g of 3,3',4,4'-tetraamino-diphenyl-disulfide are dissolved in 70 ml of alcohol and to the solution of 2.12 g of bromine cyanide dissolved in 10 ml alcohol are added. The mixture is allowed to stand overnight, whereafter the alcohol is distilled off and the residue is dissolved in water and made alkaline with sodium hydroxide. 3.0 g (90%) of the bis(2-amino-benzimidazole-5-yl-disulfide are obtained, melting at 245° C. by decomposition.

EXAMPLE 24

2.78 g of 3,3',4,4'-tetraamino-diphenyl-disulfide are dissolved in 1.7 ml. of a 37% hydrochloric acid and a solution of 0.92 g of cyanamide in 1 ml of water is added dropwise. The reaction mixture is kept for 60 minutes at a temperature of 100° C. 0.9 g of sodium hydroxide are added in the form of a 40% solution, until the ammonia evolution has ceased the mixture is heated at a temperature of 100° C. After cooling the bis(2-amino-benzimidazole-5-yl)-disulfide is precipitated. Weight: 2.70 g (81%). Melting point: 245° C. (decomposition).

EXAMPLES 25 TO 33

One proceeds according to the process of the Examples 23 or 24, using the following o-phenylene-diamine derivatives:

2,2'-dimethyl-4,4',5,5'-tetraamino-diphenyl-disulfide;
2,2'-dibutyl-4,4,',5,5'-tetraamino-diphenyl-disulfide;
2,2'-dibromo-4,4',5,5'-tetraamino-diphenyl-disulfide;
2,2'-dichloro-4,4',5,5'-tetraamino-diphenyl-disulfide;
2,2'-difluoro-4,4',5,5'-tetraamino-diphenyl-disulfide;
2,2'-di(trifluoromethyl)-4,4',5,5'-tetraamino-diphenyl-disulfide;
2,2'-dimethoxy-4,4',5,5'-tetraamino-diphenyl-disulfide;
2,2'-diphenoxy-4,4',5,5'-tetraamino-diphenyl-disulfide;
2,2'-diphenyloxy-4,4'-5,5'-tetraamino-diphenyl-disulfide.

In this way the following products are obtained:
bis(2-amino-6-methyl-benzimidazole-5-yl)-disulfide;
bis(2-amino-6-butyl-benzimidazole-5-yl)-disulfide;
bis(2-amino-6-bromo-benzimidazole-5-yl)-disulfide;
bis(2-amino-6-chloro-benzimidazole-5-yl)-disulfide;
bis(2-amino-6-fluoro-benzimidazole-5-yl)-disulfide;
bis(2-amino-6-trifluoromethyl-benzimidazole-5-yl)-disulfide;
bis(2-amino-6-methoxy-benzimidazole-5-yl)-disulfide;
bis(2-amino-6-phenoxy-benzimidazole-5-yl)-disulfide;
bis(2-amino-6-benzyloxy-benzimidazole-5-yl)-disulfide.

EXAMPLE 34

3.32 g of bis(2-amino-benzimidazole-5-yl)-disulfide are dissolved in 300 ml of pyridine and 2.0 g chloroformic acid methylester are added while cooling. The mixture is allowed to stand overnight, whereafter it is heated on a hot water-bath for 90–120 minutes. The pyridine is distilled of in vacuo and water is poured on the residue and the precipitated crystals are filtered, washed and dried. 3.4 g of the bis(2-methoxy-carbonyl-amino-benzimidazole-5-yl)-disulfide are obtained. Yield 78%. Melting point: 325° C. (decomposition).

EXAMPLE 35

3.32 g of bis-(2-amino-benzimidazole-5-yl)-disulfide are dissolved in 30 ml of methyl alcohol and to the solution 1.80 g dimethyl carbonate and 0.46 g of metallic sodium dissolved in 30 ml of methyl alcohol are added. The mixture is boiled for 1 hour. Thereafter the reaction mixture is acidified with acetic acid (pH value between 5.5–6) and the precipitated bis(2-methoxycarbonyl-aminobenzimidazole-5-yl)-disulfide is filtered off. Weight: 4.1 g (92.5%). Melting point 325° C. (decomposition).

EXAMPLE 36- TO 44

One proceeds according to the process of Examples 34 or 35 using the following bis(2-amino-benzimidazole-5-yl)-disulfide derivatives:
bis(2-amino-6-methyl-benzimidazole-5-yl)-disulfide;
bis(2-amino-6-butyl-benzimidazole-5-yl)-disulfide;
bis(2-amino-6-bromo-benzimidazole-5-yl)-disulfide;
bis(2-amino-6-chloro-benzimidazole-5-yl)-disulfide;
bis(2-amino-6-fluoro-benzimidazole-5-yl)-disulfide;
bis(2-amino-6-trifluoromethyl-benzimidazole-5-yl)-disulfide;
bis(2-amino-6-methoxy-benzimidazole-5-yl)-disulfide;
bis(2-amino-6-phenoxy-benzimidazole-5-yl)-disulfide,
bis(2-amino-6-benzyloxy-benzimidazole-5-yl)-disulfide.

In this way the following products were obtained:

bis(2-methoxycarbonyl-amino-6-methyl-benzimidazole-5-yl)-disulfide;
bis(2-methoxycarbonyl-amino-6-butyl-benzimidazole-5-yl)-disulfide;
bis(2-methoxycarbonyl-amino-6-bromo-benzimidazole-5-yl)-disulfide;
bis(2-methoxycarbonyl-amino-6-chloro-benzimidazole-5-yl)-disulfide;
bis(2-methoxycarbonyl-amino-6-fluoro-benzimidazole-5-yl)-disulfide;
bis(2-methoxycarbonyl-amino-6-trifluoromethyl-benzimidazole-5-yl)-disulfide;
bis(2-methoxycarbonyl-amino-6-methoxy-benzimidazole-5-yl)-disulfide;
bis(2-methoxycarbonyl-amino-6-phenoxy-benzimidazole-5-yl)-disulfide;

bis(2-methoxycarbonyl-amino-6-benzyloxy-benzimidazole-5-yl)-disulfide.

EXAMPLE 45

44.4 g of 2-(methoxycarbonyl-amino)-benzimidazole-5(6)-yl-disulfide are dissolved in 800 ml of hexamethylphosphoric acid triamide and while stirring vigorously, in a nitrogen atmosphere 8 g of sodium borohydride are added in 60–90 minutes at a temperature of 20°–25° C. After addition of the first parts of the reducing agent the faint yellowish color of the solution becomes brown.

After 2 hours a solution of 24.6 g of propylbromide in 600 ml of anhydrous alcohol is added and the reaction mixture is stirred in a nitrogen atmosphere for another 3 hours at room temperature. Thereafter the mixture is diluted with 1 lit. of water and the precipitated product is filtered, washed with water and recrystallized from n-propanol. 40.7 g (77%) of the 5(6)-propylthio-benzimidazolyl-2-methyl-carbamate are obtained. Melting point: 214°–215° C.

EXAMPLE 46

4.4 g of 2-(methoxycarbonyl-amino)-benzimidazole-5(6)-yl-disulfide are dissolved in 60 ml of hot dimethylformamide, whereafter the solution is cooled to room temperature and in a nitrogen atmosphere, while stirring vigorously 0.8 g of sodium borohydride are added in portions in 30 minutes. The stirring and introduction of nitrogen is continued for an additional 90 minutes and then 2.5 g of propylbromide dissolved in 50 ml of alcohol are added to the reaction mixture. The mixture is stirred for another 3 hours at room temperature and is diluted with 120 ml of water. The precipitated product is filtered, washed thoroughly with water and dried. 4.9 g of the 5(6)-propylthio-benzimidazolyl-2-methyl-carbamate are obtained.j Yield 92.5%, melting point 208°–211° C. After recrystallization from n-propanol the product melts at 215° C.

EXAMPLE 47

One proceeds according to Examples 45 or 46 but, instead of n-propylbromide, allybromide, propargylbromide, benzylchloride, 4-nitro-fluorobenzene and 2,4-dinitro-chlorobenzene are used. The following compounds are obtained:

5(6)-allylthio-benzimidazolyl-2-methylcarbamate;
5(6)-propin-2-ylthio-benzimidazolyl-2-methylcarbamate;
5(6)-benzylthio-benzimidazolyl-2-methylcarbamate;
5(6)-(4-nitrophenylthio)-benzimidazoly-2-methylcarbamate;
5(6)-(2,4-dinitrophenylthio)-benzimidazolyl-2-methylcarbamate;

EXAMPLE 48

4.4 g of 2-(methoxycarbonyl-amino)-benzimidazol-5(6)-yl-disulfide are suspended in 30 ml. of methyl alcohol and a solution of 1.12 g of potassium hydroxide in 15 ml of methyl alcohol is added. To the solution thus obtained, with continuous stirring, in a nitrogen atmosphere first 2.5 g of propylbromide and then 0.6 of sodium borohydride are added in 30 minutes at a temperature of 25° C C. in portions. The mixture is stirred for further 3 hours and then is diluted with 50 ml of water. After standing the precipitated product is filtered, washed and dried. 3 g (57%) of the crude 5(6)-propylthio-benzimidazolyl-2-methylcarbamate are obtained. Melting point after recrystallization from n-propanol is 214°–215° C. The product obtained is identical with that obtained in Examples 45 and 46.

EXAMPLE 49

4.4 g of 2-(methoxycarbonyl-amino)-benzimidazol-5(6)-yl-disulfide are suspended in 30 ml of methyl alcohol, and a hot solution of 1.12 g of potassium hydroxide in 15 ml of methyl alcohol is added in nitrogen atmosphere. To the solution obtained, 0.8 g of sodium borohydride are added at room temperature in 30–40 minutes. After stirring for 30 minutes 1.2 ml of acetic acid, then a solution of 2.5 g propylbromide in 10 ml of methyl alcohol is added to the reaction mixture. Stirring is continued for an addional 2 hours. Thereafter the mixture is diluted with 50 ml of water, and after standing for a while the precipitated product is filtered, washed and dried. 3.9 g of the 5(6)-propylthio-benzimidazolyl-2-methylcarbamate is obtained. Melting point 211°–213° C., yield 53%.

EXAMPLE 50

2.2 g of 2-(methoxycarbonyl-amino)-benzimidazol-5(6)-yl-disulfide are suspended in 20 ml of alcohol and 1.2 ml of triethylamine, then 0.8 g of 2-mercaptoethanol are added. The reaction mixture is stirred for 5 hours. Thereafter a solution of 0.56 g of potassium hydroxide in 10 ml of anhydrous alcohol and 1.3 g of propylbromide are added. Stirring is continued for further 2–3 hours at room temperature. Finally the mixture is diluted with 30 ml of water and the precipitated product is filtered, washed and dried. 1.4 g (53%) of the 5(6)-propylthio-benzimidazolyl-2-methylcarbamate are obtained. Melting point: 211°–213° C.

EXAMPLE 51

4.4 g of 2-(methoxycarbonyl-amino)-benzimidazol-5(6)-yl-disulfide are suspended in 100 ml of hot alcohol and to the suspension a solution of 1.12 g potassium hydroxide in 15 ml of water is added, then a solution of 12 g of crystalline sodium sulfide in 15 ml of water is added in portions in a nitrogen atmosphere, in 30–45 minutes. Thereafter a phenyl-diazonium-chloride solution prepared from 1.9 g of aniline and buffered with sodium acetate is added to the hot reaction mixture in 10–15 minutes. A vigorous foaming begins, which eases 15–20 minutes after dosage. The pH value of the mixture is adjusted to 6.5 and the precipitated product is filtered, washed and dried. 3.3 g (60%) of the 5(6)-phenylthio-benzimidazolyl-2-methylcarbamate are obtained. Melting point: 243° C. (decomposing).

EXAMPLE 52

2.2 g of 2-(methoxycarbonyl-amino)-benzimidazol-5(6)-yl-disulfide are dissolved in 60 ml of hot acetic acid and in a nitrogen atmosphere 0.8 g of zinc dust is added in portions. After complete dissolutions of the zinc the reaction mixture is evaporated to dryness in vacuo and is stirred in nitrogen atmosphere for 1 hour with an alcoholic potassium hydroxide solution. The reaction mixture is filtered and to the alcoholic solution 1.3 g of propylbromide are added. The reaction mixture is allowed to stand for 2 hours at room temperature and then diluted with water and the precipitated product is filtered, washed and dried. 1.8 g (68%) of the 5(6)-propylthio-benzimidazolyl-2-methylcarbamate are obtained, melting at 211°–214° C.

EXAMPLE 53

2.2 g of 2-(methoxycarbonyl-amino)-benzimidazol-5(6)-yl-disulfide are dissolved in 40 ml of alcohol containing 0.6 g of potassium hydroxide and to the hot solution, a solution of 1.0 g of glucose in 15 ml of water is added in 60 minutes. The reaction mixture is then boiled vigorously for 45 minutes and is next filtered by a pressure-filter in a nitrogen atmosphere. The alcoholic solution is cooled to room temperature and 1.3 g of propylbromide are added. After 3 hours the reaction mixture is diluted with water, the precipitated product is filtered, washed and dried. 1.6 g (60%) of the 5(6)-propylthio-benzimidazolyl-2-methylcarbamate are obtained. Melting point: 210°–213° C.

EXAMPLE 54

2.2 g of 2-(methoxycarbonyl-amino)-benzimidazol-5(6)-yl-disulfide are suspended in ethyl alcohol containing 1.6 g of potassium hydroxide and 2 g of amino-imino-methanesulfinic acid and 1 drop of an alcoholic cetyl-pyridiniumbromide solution (or hexadecyl-tributyl-phosphonium-chloride are added. The reaction mixture is boiled in a nitrogen atmosphere for 2–3 hours, and is then cooled to room temperature and 1.3 g of propylbromide are added. After 3 hours the reaction mixture is diluted with 40 ml of water and the pH value is adjusted to 6, the precipitated product is filtered, washed and dried. 2.1 g (79%) of the 5(6)-propylthio-benzimidazolyl-2-methylcarbamate are obtained.

MELTING POINT: 210°–212° C.

EXAMPLES 55 TO 66

In a manner analogous to that of Examples 45 to 54 by using the following starting materials the following compounds of the Formula I are prepared ($R^1$ is always methoxycarbonyl):

| Example | $R^2$ | $R^4$ | Mp °C. | |
|---|---|---|---|---|
| 55 | fluorine | n-propyl | 252–253 | |
| 56 | chlorine | n-propyl | 266–269 | |
| 57 | chlorine | benzyl | 234–236 | |
| 58 | chlorine | allyl | 203–205 | |
| 59 | chlorine | propinyl | 305–307 | |
| 60 | chlorine | ethyl | 237–238 | |
| 61 | chlorine | cyclohexyl | 294–295 | |
| 62 | bromine | n-propyl | 191–193 | |
| 63 | methyl | n-propyl | 230–232 | (d) |
| 64 | methoxy | n-propyl | 296–298 | |
| 65 | butyl | n-propyl | 202–204 | |
| 66 | trifluoromethyl | n-propyl | 252 | |

What we claim is:

1. A compound of the formula

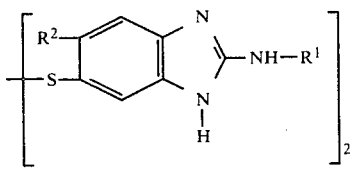

wherein $R^1$ is hydrogen or —$COOR^5$;

$R^5$ is $C_1$ to $C_4$ alkyl;

$R^2$ is hydrogen, halogen, $C_1$ to $C_6$ alkyl, trifluoromethyl or —$OR^3$; and $R^3$ is $C_1$ to $C_4$ alkyl, phenyl, naphthyl, phenyl-$C_1$ to $C_4$ alkyl or naphthyl-$C_1$ to $C_4$ alkyl, where the phenyl or naphthyl moiety is unsubstituted or substituted by halogen, lower alkyl, lower alkoxy, lower alkylthio, carboxy, nitro, hydroxy, cyano, $C_1$ to $C_4$ alkylsulfinyl or $C_1$ to $C_4$ alkylsulfonyl; or a pharmaceutically acceptable salt thereof.

2. A compound of the formula:

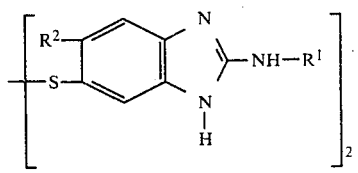

wherein $R^1$ is hydrogen or -$COOR^5$ $R^5$ is $C_1$ to $C_4$ alkyl $R^2$ is hydrogen, halogen, $C_1$ to $C_6$ alkyl, trifluoromethyl or —$OR^3$; and $R^3$ is $C_1$ to $C_4$ alkyl, phenyl or benzyl; or a pharmaceutically acceptable salt thereof.

3. A compound of the formula:

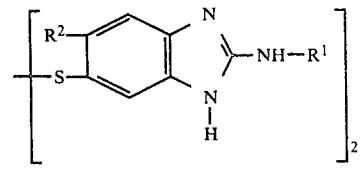

wherein $R^1$ is hydrogen or methoxycarbonyl;

$R^2$ is hydrogen, chlorine, bromine, fluorine, trifluoromethyl, methyl, butyl or —$OR^3$; and $R^3$ is methyl, phenyl or benzyl; or a pharmaceutically acceptable salt thereof.

4. A compound selected from the group consisting of:
bis-(2-amino-benzimidazole-5-yl)-disulfide;
bis-(2-amino-6-methyl-benzimidazole-5-yl)-disulfide;
bis-(2-amino-6-butyl-benzimidazole-5-yl)-disulfide;
bis-(2-amino-6-bromo-benzimidazole-5-yl)-disulfide;
bis-(2-amino-6-chloro-benzimidazole-5-yl)-disulfide;
bis-(2-amino-6-fluoro-benzimidazole-5-yl)-disulfide;
bis-(2-amino-6-trifluoromethyl-benzimidazole-5-yl)-disulfide;
bis-(2-amino-6-methoxy-benzimidazole-5-yl)-disulfide;
bis-(2-amino-6-phenyloxy-benzimidazole-5-yl)-disulfide;
bis-(2-amino-6-benzyloxy-benzimidazole-5-yl)-disulfide;
bis-(2-methoxycarbonylamino-benzimidazole-5-yl)-disulfide;
bis-(2-methoxycarbonylamino-6-methyl-benzimidazole-5-yl)-disulfide;
bis-(2-methoxycarbonylamino-6-butyl-benzimidazole-5-yl)-disulfide;
bis-(2-methoxycarbonylamino-6-bromo-benzimidazole-5-yl)-disulfide;
bis-(2-methoxycarbonylamino-6-chloro-benzimidazole-5-yl)-disulfide;
bis-(2-methoxycarbonylamino-6-fluoro-benzimidazole-5-yl)-disulfide;
bis-(2-methoxycarbonylamino-6-trifluoromethyl-benzimidazole-5-yl)-disulfide;

bis-(2-methoxycarbonylamino-6-methoxy-benzimidazole-5-yl)-disulfide;

bis-(2-methoxycarbonylamino-6-phenoxy-benzimidazole-5-yl)-disulfide; and bis-2-methoxycarbonylamino-6-benzyloxy-benzimidazole-5-yl)-disulfide;

or a pharmaceutically acceptable salt thereof.

5. A fungicidal composition comprising as active ingredient an effective amount of the compound defined in claim 1 or a pharmaceutically acceptable salt thereof in admixture with a suitable inert solid or liquid carrier or diluent.

6. An anthelmintic composition for human or veterinary use comprising as active ingredient an effective amount of the compound defined in claim 1 or a pharmaceutically acceptable salt thereof in admixture with a suitable inert solid or liquid carrier or diluent.

7. A compound of the formula:

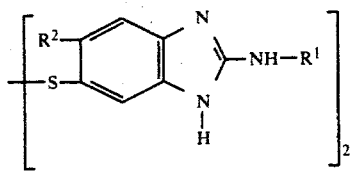

wherein
$R^1$ is hydrogen or —$COOR^5$;
$R^5$ is $C_1$ to $C_4$ alkyl; and
$R^2$ is hydrogen or halogen; or a pharmaceutically acceptable salt thereof.

8. The compound defined in claim 7 which is bis-(2-methoxy-carbonylamino-benzimidazole-5-yl)-disulfide or a pharmaceutically acceptable salt thereof.

9. The compound defined in claim 7 which is bis-(2-methoxy-carbonylamino-6-chloro-benzimidazole-5-yl)-disulfide or a pharmaceutically acceptable salt thereof.

10. The compound defined in claim 7 which is bis-(2-methoxy-carbonylamino-6-fluoro-benzimidazole-5-yl)-disulfide or a pharmaceutically acceptable salt thereof.

11. A method of treating an anthelmintic infection in animals which comprises administering to the animal a pharmaceutically effective amount of the compound defined in claim 1 or a pharmaceutically acceptable salt thereof.

12. A method of treating a fungal infection in plants which comprises administering to the plant a pharmaceutically effective amount of the compound defined in claim 1 or a fungicidally acceptable salt thereof.

* * * * *